(12) United States Patent
Ulrich et al.

(10) Patent No.: US 7,242,308 B2
(45) Date of Patent: *Jul. 10, 2007

(54) BED STATUS INFORMATION SYSTEM FOR HOSPITAL BEDS

(75) Inventors: Daniel J. Ulrich, Cincinnati, OH (US); Matthew W. Weismiller, Batesville, IN (US); Tom Scott, Indianapolis, IN (US); Bob Jennings, Annandale, VA (US); Julie Myers, Indianapolis, IN (US); Joe Novak, Batesville, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/126,609

(22) Filed: May 11, 2005

(65) Prior Publication Data

US 2005/0219059 A1 Oct. 6, 2005

Related U.S. Application Data

(63) Continuation of application No. 10/083,192, filed on Feb. 26, 2002, now Pat. No. 6,897,780, which is a continuation of application No. 09/711,641, filed on Nov. 13, 2000, now Pat. No. 6,362,725, which is a continuation of application No. 08/985,757, filed on Dec. 15, 1997, now Pat. No. 6,147,592, which is a continuation of application No. 08/511,701, filed on Aug. 4, 1995, now Pat. No. 5,699,038, which is a continuation-in-part of application No. 08/090,804, filed on Jul. 12, 1993, now Pat. No. 5,561,412.

(51) Int. Cl.
G08B 23/00 (2006.01)
G08B 5/22 (2006.01)
H04Q 1/30 (2006.01)

(52) U.S. Cl. .............. 340/573.1; 340/286.07; 340/539.12; 340/539.13; 340/539.16; 340/539.17; 340/825.72

(58) Field of Classification Search .............. 340/573.1, 340/286.07, 539.12, 539.13, 539.16, 539.17, 340/825.72
See application file for complete search history.

(56) References Cited

U.S. PATENT DOCUMENTS

| | | | |
|---|---|---|---|
| 3,599,199 | A | 8/1971 | Bunting |
| 3,913,153 | A | 10/1975 | Adams et al. |
| 4,183,015 | A | 1/1980 | Drew et al. |
| 4,216,462 | A | 8/1980 | McGrath et al. |

(Continued)

Primary Examiner—Julie Bichngoc Lieu
(74) Attorney, Agent, or Firm—Barnes & Thornburg LLP

(57) ABSTRACT

A bed monitoring system that remotely monitors a patient bed. The bed monitoring system comprises a bed status system and a master station. The bed status system is coupled to the patient bed and is configured to monitor at least one condition of the bed, and to generate a bed message indicating the status of the monitored condition. The master station, remote from the patient bed, is operatively coupled to the bed status system to receive bed status information. The bed message can include a bed identifier, bed type identifier, patient exit detection signal, bed occupied signal, or various other status signals. The system can also include locating stations that receive the bed messages from any beds within its monitored location, and generates a station message including information from the bed messages. The master station receives the station messages and can determine the status and location of any bed.

33 Claims, 7 Drawing Sheets

U.S. PATENT DOCUMENTS

| | | | |
|---|---|---|---|
| 4,237,344 A | 12/1980 | Moore | |
| 4,279,433 A | 7/1981 | Petaja | |
| 4,356,475 A | 10/1982 | Neumann et al. | |
| 4,495,495 A | 1/1985 | Ormanns et al. | |
| 4,539,560 A | 9/1985 | Fleck et al. | |
| 4,593,273 A | 6/1986 | Narcisse | |
| 4,601,064 A | 7/1986 | Shipley | |
| 4,680,790 A | 7/1987 | Packard et al. | |
| 4,814,751 A | 3/1989 | Hawkins et al. | |
| 4,833,452 A | 5/1989 | Currier | |
| 4,853,692 A | 8/1989 | Wolk et al. | |
| 4,899,135 A | 2/1990 | Ghahariian | |
| 4,907,845 A * | 3/1990 | Wood | 340/573.4 |
| 4,947,152 A * | 8/1990 | Hodges | 340/573.4 |
| 4,967,195 A | 10/1990 | Shipley | |
| 4,998,939 A | 3/1991 | Potthast et al. | |
| 5,006,830 A | 4/1991 | Merritt | |
| 5,062,151 A | 10/1991 | Shipley | |
| 5,065,154 A | 11/1991 | Kaiser et al. | |
| 5,086,290 A | 2/1992 | Murray et al. | |
| 5,266,944 A | 11/1993 | Carroll et al. | |
| 5,291,399 A | 3/1994 | Chaco | |
| 5,357,254 A | 10/1994 | Kah, Jr. | |
| 5,396,224 A | 3/1995 | Dukes et al. | |
| 5,396,227 A | 3/1995 | Carroll et al. | |
| 5,416,695 A | 5/1995 | Stutman et al. | |
| 5,455,560 A | 10/1995 | Owen | |
| 5,461,390 A | 10/1995 | Hoshen | |
| 5,465,082 A | 11/1995 | Chaco | |
| 5,475,367 A | 12/1995 | Prevost | |
| 5,515,426 A | 5/1996 | Yacenda et al. | |
| 5,537,459 A | 7/1996 | Price et al. | |
| 5,548,637 A | 8/1996 | Heller et al. | |
| 5,561,412 A | 10/1996 | Novak et al. | |
| 5,568,119 A | 10/1996 | Schipper et al. | |
| 5,588,005 A | 12/1996 | Ali et al. | |
| 5,594,786 A | 1/1997 | Chaco et al. | |
| 5,621,388 A | 4/1997 | Sherburne et al. | |
| 5,635,907 A | 6/1997 | Bernard et al. | |
| 5,636,245 A | 6/1997 | Ernst et al. | |
| 5,650,769 A | 7/1997 | Campana, Jr. | |
| 5,650,770 A | 7/1997 | Schlager et al. | |
| 5,682,139 A | 10/1997 | Pradeep et al. | |
| 5,686,888 A | 11/1997 | Welles, II et al. | |
| 5,686,902 A | 11/1997 | Reis et al. | |
| 5,689,229 A | 11/1997 | Chaco et al. | |
| 5,691,980 A | 11/1997 | Welles, II et al. | |
| 5,699,038 A | 12/1997 | Ulrich et al. | |
| 5,705,980 A | 1/1998 | Shapiro | |
| 5,708,421 A | 1/1998 | Boyd | |
| 5,731,757 A | 3/1998 | Layson, Jr. | |
| 5,742,237 A | 4/1998 | Bledsoe | |
| 5,751,246 A | 5/1998 | Hertel | |
| 5,760,704 A | 6/1998 | Barton et al. | |
| 5,793,290 A | 8/1998 | Eagleson et al. | |
| 5,808,564 A | 9/1998 | Simms et al. | |
| 5,812,056 A | 9/1998 | Law | |
| 5,822,418 A | 10/1998 | Yacenda et al. | |
| 5,822,544 A | 10/1998 | Chaco et al. | |
| 5,838,223 A | 11/1998 | Galant et al. | |
| 6,009,333 A | 12/1999 | Chaco | |
| 6,147,592 A | 11/2000 | Ulrich et al. | |
| 6,259,355 B1 | 7/2001 | Chaco et al. | |
| RE37,531 E | 1/2002 | Chaco et al. | |
| 6,362,725 B1 | 3/2002 | Ulrich et al. | |

* cited by examiner

INFO-BED STATUS

| ROOM | EXIT | RAIL DOWN | BRAKES | HEIGHT UP | SURFACE COMFORT |
|------|------|-----------|--------|-----------|-----------------|
| 103A | ✓    | ✓         |        |           |                 |

WAITING CALLS: 0

| ROOM | NAME | TYPE |
|------|------|------|

11:26:23
WED DEC 7

ANSWER | CALL | PAGE | LOCATE | INFO | SETUP | LEARN

FIG. 8

BED STATUS INFORMATION SYSTEM FOR HOSPITAL BEDS

RELATED APPLICATIONS

This application is a continuation of U.S. patent application Ser. No. 10/083,192 filed on Feb. 26, 2002 now U.S. Pat. No. 6,897,780; which is a continuation of U.S. patent application Ser. No. 09/711,641 filed on Nov. 13, 2000, now U.S. Pat. No. 6,362,725; which is a continuation of U.S. patent application Ser. No. 08/985,757 filed on Dec. 15, 1997, now U.S. Pat. No. 6,147,592; which is a continuation of U.S. patent application Ser. No. 08/511,701 filed on Aug. 4, 1995, now U.S. Pat. No. 5,699,038; which is a continuation-in-part of U.S. patent application Ser. No. 08/090,804 filed on Jul. 12, 1993, now U.S. Pat. No. 5,561,412.

FIELD OF THE INVENTION

The present invention relates to hospital beds, and in particular, to a bed status information system capable of remotely providing patient bed information to attending medical personnel.

BACKGROUND OF THE INVENTION

Nurses and other attending staff in a hospital ward or hospital wing work under conditions involving high pressure, stress and long hours. These caregivers must remain alert to respond to patient needs, in both emergency and non-emergency situations. Due to economic practicalities and the ever-increasing costs of medical care, it is necessary to make the most efficient use of nurses and staff on call in a hospital wing, particularly at night when nurse and staff levels are maintained at a minimum.

On the other hand, a desire to optimize the efficiency of nurse and staff personnel is of secondary importance relative to the primary objective, that of providing a high level of medical care to a patient. If nurse and staff levels are reduced for the sake of efficiency without any corresponding simplification of duties and responsibilities, the level of patient care will decrease. Therefore, it is desirable to maximize the efficiency of nurses and staff on call in a hospital wing, but to do so in a manner which does not increase the work load or stress levels of these professional caregivers nor decrease the level of patient care.

One approach to maximizing the efficiency of nurses and other hospital staff involves the use of a location and identification system to continuously monitor the various locations of these persons. For instance, White U.S. Pat. No. 4,275,385 discloses a personnel locating system where individuals to be located wear infrared transmitters, and each transmitter transmits a pulse-coded signal which corresponds to the identity of the wearer. A number of other U.S. Patents also disclose personnel locating or monitoring systems which purport to improve upon the system disclosed in the White patent. These improvements relate to the mechanics of signal detection, or the organization, maintenance and retrieval of stored information for making reports. Even with such automated communication systems that allow retrieval of information at a central, remote location, certain traditional tasks still have to be handled locally at the patient location and require the hospital personnel to physically be present with the patient to visually observe the patient or the status of the equipment utilized by the patient.

One such traditional task of hospital nurses and staff is to monitor the condition or status of a large number of hospital patient beds. Currently available hospital beds are equipped with a variety of mechanical and electrical systems related to patient care, and these systems must be monitored to ensure proper care. For example, the condition of the mattress surface as well as the shape of that surface must often be monitored by the attending staff to ensure that the patient is in the proper position and will not suffer from skin breakdown or other ailments due to an extended time spent in the bed. Furthermore, it is often necessary to know whether the patient is actually in the bed or has exited the bed, despite the request of the attending personnel. Still further, various other mechanical bed conditions must also be monitored to determine that they are working properly or are in a desired state. With conventional beds, the status of the bed is revealed at either headboard or footboard consoles or in a console located on the wall inside of a patient room. Therefore, monitoring the bed status requires attendance of personnel within the room to locally view and interpret the various bed consoles. Not only is such a task time consuming, but certain bed status conditions, such as whether the patient is still in the bed, should be responded to as soon as possible rather than at some predetermined interval that corresponds with scheduled patient visits by the attending personnel.

It is also important for hospital administration and personnel to know whether patient beds are occupied or unoccupied and their locations in the facility. Knowing where a patient bed is located, its bed type and whether it is clean, dirty or occupied allows a facility to make more informed decisions about where to locate a new patient, and to more efficiently utilize its resources.

SUMMARY OF THE INVENTION

The bed monitoring system claimed in the present application remotely monitors the status of a patient bed. The bed monitoring system comprises a bed status system coupled to the patient bed and a master station remote from the patient bed. The bed status system monitors at least one condition of the patient bed to which it is coupled, and generates a bed status message indicating the status of the monitored condition. The master station is operatively coupled to the bed status system to receive bed status information related to the bed status message.

The bed status message can include one or more of various status indicators, including, but not limited to, a bed identifier unique to the patient bed to which it is coupled, a bed type identifier, a patient exit detection signal, and a bed occupied signal. This status information being made available at the master station through the bed status messages sent by the bed status system.

The bed status system can be configured to monitor a plurality of monitored conditions, and the bed status message indicating the status of at least one condition of the plurality of monitored conditions. The bed status system can be configured to generate content for the bed status message based on a selector signal, the selector signal indicating which of the conditions of the plurality of monitored conditions of the patient bed are to be included in the bed status message. The selector signal may be generated by the master station to receive only status information of interest.

The bed monitoring system can also include locating stations located in each of a plurality of monitored locations. Each locating station receives the bed status messages from any patient beds within the monitored location associated with the locating station, and generates a station status message including information from the bed status messages and indicating the location of the locating station. The master station receives the station status messages generated by the locating stations and can determine the location of any patient bed.

The master station can also include a display device for visually displaying the bed status information received from the bed status system.

The above and other features and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention and, together with a general description of the invention given above, and the detailed description of the embodiments given below, serve to explain the principles of the invention and to enable a person of ordinary skill in the art to practice the invention.

FIG. 8 is an electrical schematic which shows electrical connections among components of the wall interface unit for the bed status system and patient/nurse communication system in accordance with this invention.

DETAILED DESCRIPTION OF SPECIFIC EMBODIMENTS

In a preferred embodiment of the present invention, a patient bed status system 11 is integrated with a patient/nurse communication system 10, such that, in addition to providing patient bed status information, the integrated system also provides information regarding the location and identities of patients and attending personnel, such as nurses. Therefore, an overview description of the patient/nurse communication system 10 and its functioned features as well as is integration with the bed status System II is helpful in understanding the operation of the bed status System II and its overall effect in enhancing patient care. A more detailed description of the patient/nurse communication system is provided in the parent U.S. patent application Ser. No. 08/090,804 entitled "Patient/Nurse Call System", filed on Jul. 12, 1993, which application is incorporated by reference herein in its entirety.

Integrated System

Figure 1:
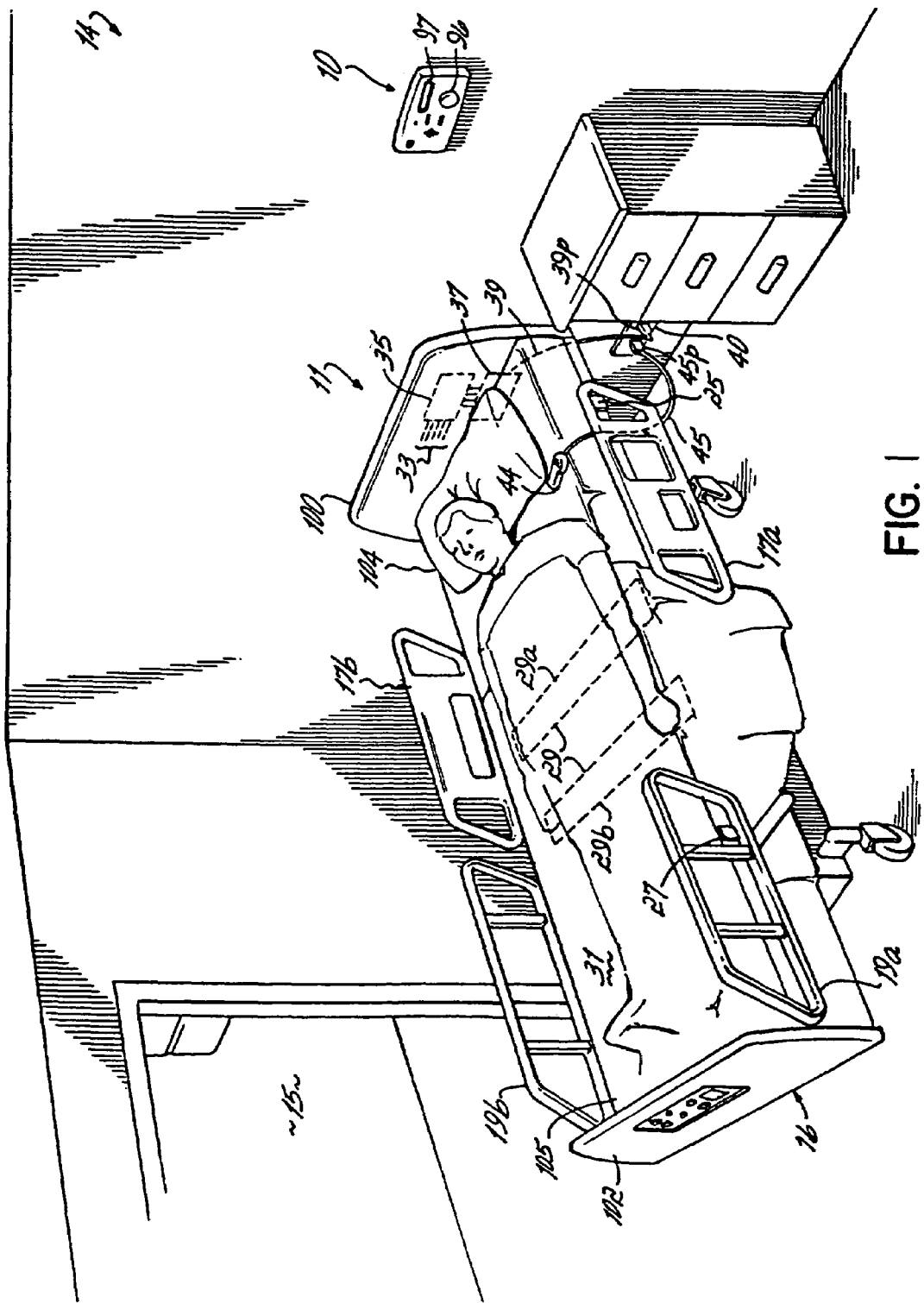
FIG. 1 is a perspective view of a hospital room which illustrates one patient bed in a patient room and the physical arrangement of various components of the bed status system in accordance with this invention.

FIG. 1 shows the physical layout of some of the components of the bed status 11 system, which is integrated with a patient/nurse call system 10 in accordance with a preferred embodiment of the invention. While bed status system 11 provides bed status information, the patient/nurse communication system 10 organizes, stores, maintains and facilitates retrieval of bed status information, along with the various non-bed calls placed in a hospital wing or ward, thereby optimizing communication capabilities among nurses and patients 12.

More specifically, FIG. 1 shows a patient room 14 accessible from a hall 15 of the hospital wing, and a patient bed 16 located in the room 14. While only one bed is shown, the invention also contemplates semi-private patient rooms 14, wherein two or more patient beds 16 are used. Patient bed 16 is equipped with a variety of mechanical and electrical systems to assist hospital personnel in patient care. The state or condition of each of these systems is detected by the present invention. For example, patient bed 16 includes headrails 17a, 17b and footrails 19a, 19b for containing a patient within the bed. The rails have an up or latched position, as indicated, by headrail 17b, and a down or unlatched position as indicated by headrail 17a. Each headrail 17a, 17b or footrail 19a, 19b of patient bed 16 is equipped with a latch sensor, such as headrail latch sensor 25 and footrail latch sensor 27 to detect whether the respective rails are in the latched or unlatched position.

Furthermore, bed 16 is equipped with a patient exit detection system which includes pressure sensitive sensor strips 29 to detect whether the patient 12 has exited the bed or is still in the bed. The patient exit detection system may be armed or disarmed and a sensor (not shown in FIG. 1) indicates whether the system is armed. Other bed system conditions are also detected on bed 16 by various sensor systems (See FIG. 4). For example, in one embodiment of the invention, bed 16 is equipped with a sensor to indicate whether the bed break is set, a sensor to indicate whether the bed is at its lowest position, and a sensor to indicate whether the mattress 31 is in a particular firmness mode to enhance the comfort of the patient. Furthermore, other various features and functions of the bed might be monitored in accordance with the principles of the present invention. One example of a suitable bed for use with the bed status system 11 of the invention is the Advance 2000.RTM. bed available from Hill-Rom.RTM. of Batesville, Ind.

The various sensed bed conditions are associated with sensor signals, and the signals are presented via hard wire connections 33 to a bed interface board 35. Interface board 35 is connected through a junction box 37 to a serial cable 39 and plug 39p which, in turn, connects to a wall interface unit 40, which couples the bed status information to a patient/nurse communication system 10. The operation of the bed interface board 35 and the wall interface unit 40 is described in greater detail hereinbelow.

The Patient/Nurse Communication System Hardware

As part of the patient/nurse communication system 10 utilized with the present invention, a patient station 41 is mounted to a head wall of the patient room 14 as shown in FIG. 1. The patient station 41 is connected by a hardwire connector 43 (see FIG. 2) to wall interface unit 40, with connector 43 located behind the headwall of the room 14. A pillow unit 44, on bed 16, connects via cable 45 to a bed outlet or plug 45p of the wall interface unit 40. The pillow unit 44 is described in greater detail in the parent application entitled "Patient/Nurse Call System" referenced above. Additionally, cable 39 plugs into a bed outlet or plug 39p of the interface unit 40, while a second end of the cable 39 is electrically coupled to bed interface board 35 through junction box 37.

Figure 2:
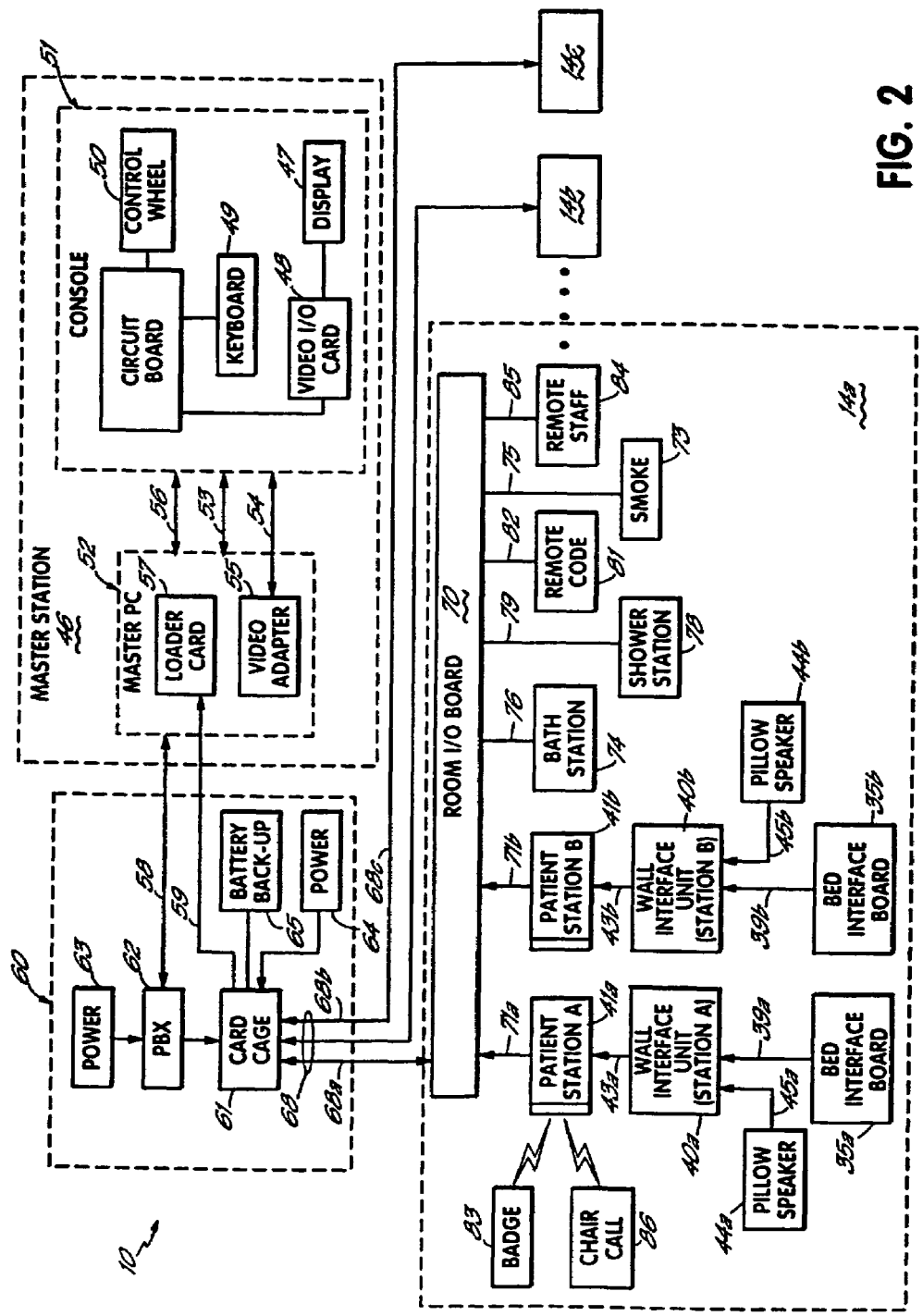
FIG. 2 is a schematic which depicts the electrical interconnections among the components and stations of a patient/nurse communication system utilized with the bed status system of this invention.

FIG. 2 schematically illustrates electrical connections among hardware components according to an embodiment of the patient/nurse communication system 10 to be utilized with the bed status system 11 of the present invention. More specifically, FIG. 2 shows a master station 46 which interconnects with all of the patient stations 41. At the master station 46, the system 10 stores location information about nurses, information about hospital calls, information about hospital beds in use (provided by bed status system 11), the status of the hospital beds in use, instructions on how to operate system 10, and a number of other features. The master station 46 classifies and displays the hospital calls according to priority status and according to time received. When the calls are retrieved by the patient stations 41, they are retrieved in this same order.

Structurally, the master station 46 includes a color display 47, a video I/O card 48, a keyboard 49, a control wheel 50, and an acoustical speaker and a handset (not shown) which interconnect with a master, station console 51. The master station console 51 serves as the interface between these components and a master station personal computer 52 which preferably includes memory, a hard drive (with at least 4 M byte memory capacity), a floppy disc drive, parallel ports, serial ports and a power supply (not shown). A keyboard cable 53 interconnects the master station console 51 with a video adapter 55. A coaxial cable 54 supplies electrical power to master console 51 and these components, and cable 54 interconnects the video interface 48 with the video adapter 55, via master station console 51. Another electrical cable 56 interconnects the master station console 51 with a loader card 57 in the personal computer 52, and cable 56 includes two audio (2B+2D) channels in a single, eight conductor cable. The master station 46 is physically located at a staff station in the hospital wing, a nurse station of the hospital wing or a general office for the hospital wing.

The personal computer 52 of the master station 46 interconnects via cables 58 and 59 to signal processing components of the system, which are preferably located within an equipment closet or cabinet 60 in the hospital wing. Cable 59 includes three audio (2B+2D) channels in a single, eight conductor cable and cable 58 is an RS-232 line. The components located within the equipment cabinet 60 include a card cage 61 for locating power distribution cards (not shown) and an expandable private branch exchange (or "PBX") 62, which is preferably a component manufactured by Comdial Corporation of Charlottesville, Va., under the trademark DXP.

Basically, this DXP is a voice/data switch, and it contains the necessary hardware and software to allocate point-to-point audio links and to distribute data in the form of messages from the master station 46 to the patient stations 41, and vice versa.

The master station 46 occupies three audio stations. A single DXP serving as the PBX 62 can connect five 16-channel cards, or seventy-seven patient stations 41 plus the master station 46. Each power distribution card in the card cage 61 can connect a maximum of sixteen audio stations. An expanded PBX 62 and cabinet 60 can allow a total of one hundred and ninety-two audio stations or one hundred and eighty nine patient stations 41 plus one master station 46 (which requires three audio lines). This expanded capability requires one PBX (type DXP) 62, a DXP expansion cabinet (not shown) and twelve power distribution cards. Eventually, interconnection of additional master stations 46 could further expand the capability of the system 10.

A power supply 63 supplies electrical power to the PBX 62. A power supply 64 and a battery backup 65 connect to card cage 61 and supply electrical power to the other components in the cabinet 60.

An electrical cable 68 connects one of the power distribution cards of the card cage 61 to a patient room 110 board 70. Each hospital room 14 in the hospital wing includes an I/O board 70, and this I/O board 70 includes multiple connections and inputs for generating calls from the room 14. FIG. 2 shows patient room 14a connected to card cage 61 via cable 68a, and patient rooms 14b and 14c connected to card cage 54 via cables 68b and 68c, respectively.

The I/O board 70 and its interconnected components comprise the intra-room network to which bed status information is provided in accordance with the present invention. Communication among components connected to I/O board 70 occurs over two wire, half duplex, multidrop EIA RS-485 standard, with message exchange being peer to peer. Any device on the intra-room network can send data to any other device without waiting for a poll. The intra-room network is not transformer isolated.

Each patient station 41 interfaces with the PBX 62 over a two-wire twisted pair network (Motorola UDLT 2B+2D), and messages are transmitted and received between the stations 41 and the PBX 62 over the D-channel. Messages received by the PBX 62 from the patient stations 41 are transmitted to the master station PC 52, and messages received by patient stations 41 originate at the master station PC 52. Patient stations 41 cannot send messages directly to each other. A patient station 41 and/or the master station PC 52 can transmit a message at any time. At the master station PC 52, a COMDIAL-supplied library called the ENTERPRZ handles the interface with the PBX 62. All messages that the system 10 wishes to pass to a patient station 41 are converted to a form that the ENTERPRZ library can accept. A function of the ENTERPRZ library is to pass messages to stations 41 on the network. The destination address is also passed as part of this function. The ENTERPRZ library then embeds this information into the library's own link-level protocol, with the library's own control information, including destination, address and checksum, etc., and sends the information as a packet to the PBX 62.

With respect to patient room 14a shown in FIG. 2, patient stations designated 41a and 41b, for example, connect to the I/O board 70 via cables 71a and 71b, respectively. Wall interface units 40a and 40b connect to patient stations 41a and 41b via cables 43a and 43b, respectively. Cable 39a interconnects a bed interface board 35a to the wall interface unit 40a, and cable 45a connects the pillow unit 44a to the wall interface unit 40a. Patient station 41b includes similar connections.

A smoke alarm 73 is connected to board 70 via line 75. Additionally, a bath, or bathroom station 74 connects to I/O board 70 via line 76. A shower station 78 connects to I/O board 70 via line 79. A remote code station 81 connects to I/O board 70 via line 82. Remote staff station 84 connects to I/O board 70 via line 85. Smoke alarm, 73, bath station 74, shower station 78, remote code station 81 and remote staff station 84 generate various signal calls associated with the room area or device, to the system 10 from patient room 14a. The calls are assigned a certain priority with respect to the gravity of the condition. For example, a smoke alarm call will certainly want to be given a high priority than say a shower call or a bed status message. Furthermore, as discussed in the Patient/Nurse Call System application, a locator badge 83 or chain call device 86 may be electrically coupled to I/O board 70.

Figure 3:
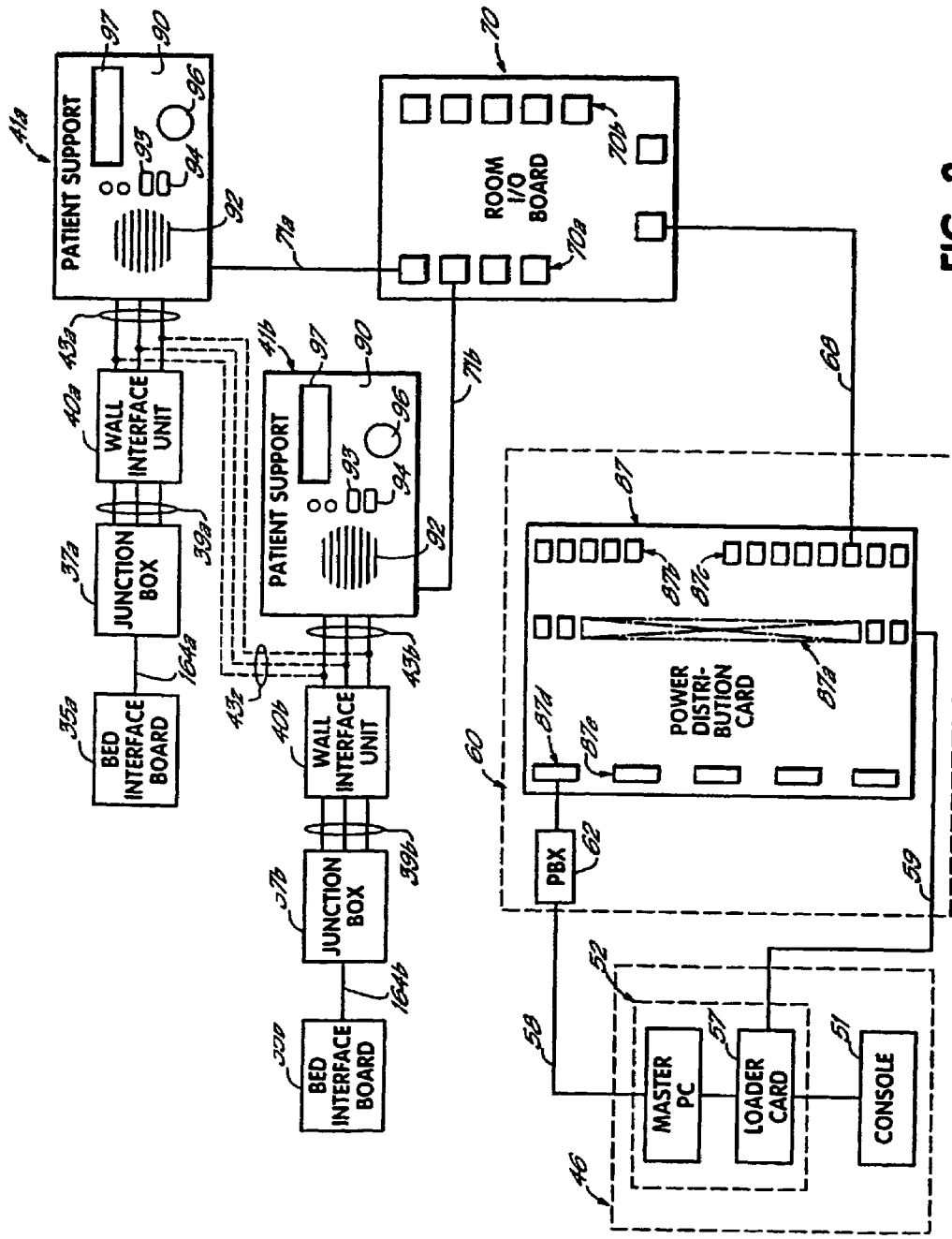
FIG. 3 is a schematic which depicts the electrical interconnections and components in a semi-private patient room utilizing the bed status system of this invention integrated with a patient/nurse communication system.

FIG. 3 is a schematic wiring diagram which shows the connections between the master station 46 and a patient room 14, but in somewhat more detail than FIG. 2. More specifically, FIG. 3 shows one of the power distribution cards 87 housed within card cage 61 (FIG. 2). Each power distribution card 87 includes sixteen (16) one-channel ports 87a, five three-channel ports 87b, eight two-channel ports 87c, a data port 87d which connects to the PBX 62, and four parallel power ports 87e. Distribution card 87 also includes a plurality, preferably 16, one-amp fuses (not shown) with each fuse corresponding to one of the single channel ports 87a. Preferably, cable 59 connects the bottommost of the single channel ports 87a to the loader card 57. In this configuration, the two lowest two-channel ports 87c cannot be used. Moving upwardly from the bottommost of the one-channel ports 87a, the next three ports are designated loader, master voice, and master monitor. The uppermost of the one-channel ports 87a is designated as a booster port.

The ports of the power distribution card 87 designate the addresses for the patient stations 41. Between the power distribution cards 87 and the various patient stations 41 within the room 14, i.e., the intra-room network, the call signals and nurse information signals do not include an address or a location signal. When calls are generated within the patient rooms 14, each call is routed to the distribution card 87 via the port designated for that specific patient station 41, and the signal is further conveyed from the power distribution card 87 to the master station 46, but with a signal address appended thereto by the PBX 62 to designate the specific station 41. Signalling between the PBX 62 and the master station 46 is via a serial data string on an RS-232 line, and each data string includes call information or bed status information combined with location information related to a particular patient station 41 associated with the call or the bed 16. The interconnection between the loader card 57 and the bottommost of the single channel ports 87a is used to download software instructions from the master station 46 to the I/O boards 70 and the stations 41. This feature will be described in more detailed in a later section.

As shown in FIG. 3, the I/O board 70 for a patient room 14 provides an interface between the power distribution cards 87 and the stations 41. More specifically, each I/O board 70 includes a plurality of ports 70a, each of which may be connected via a cable 71 to a patient station 41. As illustrated by the dashed lines 43z in FIG. 3, several bed interface boards 35 and wall interface units 40 may share a common patient station 41b to save duplication and costs. In such a case, station 41a and line 71a could be eliminated. Additional output ports 70b are configured to be connectable to other devices such as a hall unit (not shown) which is discussed in greater detail in the "Patient/Nurse Call System" parent application. Ports 70a or 70b may also be used for one or more additional stations such as a bath station 74, a shower station 78, a remote code station 81 or a remote staff station 84, depending upon the needs of the particular hospital wing (FIG. 2).

Figure 6:
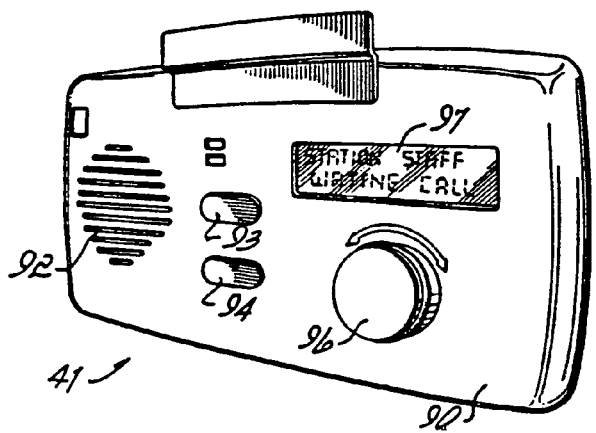
FIG. 6 is a perspective view of a patient station for a patient/nurse communication system which incorporates the bed status system of this invention.

FIG. 6 shows a perspective view of one embodiment of the patient station 41. The patient station 41 includes a molded housing 90 which connects to the head wall, preferably by screws. An audio speaker 92 resides on the left side of the housing 90. Pushbutton 93 generates a staff emergency call, and pushbutton 94 cancels the call. Control wheel 96 operates in conjunction with a display 97 to control retrieval of information from the master station 46 for display at the patient station 41. Preferably, the display 97 is a two-line by sixteen character LCD display. Rotation and depression of wheel 96 allows cursor access to various information associated with the patient station 41 as described in greater detail in the parent application entitled "Patient/Nurse Call System".

Bed Status System Hardware

Figure 4:
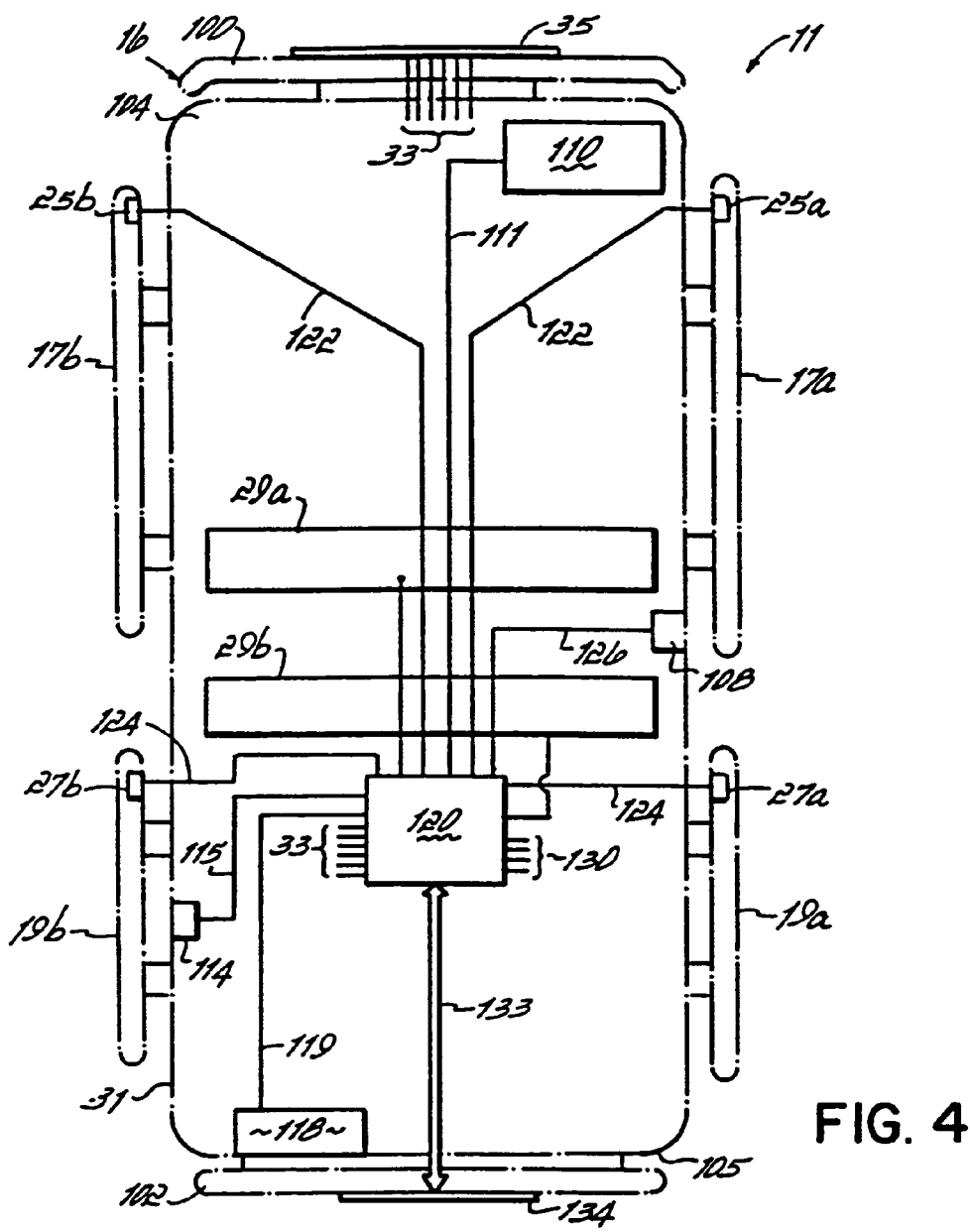
FIG. 4 is a top diagrammatic view of a patient bed configured with components of the bed status system of the invention.

FIG. 4 illustrates a hospital bed 16 incorporating the bed status system 11 of the invention. The bed 16 includes a headboard 100, a footboard 102, head siderails or headrails 17a, 17b, foot siderails or footrails 19a, 19b, and a patient mattress 31 having head and foot ends 104 and 105, respectively. The mattress 31 preferably is inflatable and can be raised, lowered or anchored. Bed 16 includes a patient exit or bed exit detection system as discussed above, including parallel pressure pads 29a, 29b which detect the pressure of a patient body 12 in the bed to indicate whether the bed is occupied or has been exited (See FIG. 1).

Bed 16 also includes various mechanical/electrical systems and a plurality of sensors which are associated with the mechanical/electrical systems on the bed and sense various status conditions of the bed 16. The sensed conditions are processed and sent to master station 46 for visual display to hospital personnel in accordance with the invention. For example, Bed 16 includes a sensor 108 electrically coupled to pressure pads 29; 3 and 29b for indicating that bed 16 has been exited by the patient. Sensor 108 also provides an indication that the bed exit detection system has been armed and is ready to detect that the bed has been exited by the patient.

Bed 16 includes sensors 25a, 25b and 27a, 27b associated with the headrails 17a, 17b and footrails 19a, 19b, respectively. The sensors 25a, 25b, and 27a, 27b detect whether one or more of the headrails or siderails are in a down or unlatched position (See FIG. 1).

Furthermore, bed 16 includes sensor 110 which senses that the bed is not in a down or lowermost position. Sensor 114 senses that the brake (not shown) on the bed 16 is not set. Sensor 118 is coupled to the inflatable mattress 31 for sensing the comfort mode of the mattress. For example, inflatable mattresses often have different levels of firmness, depending upon the condition of the patient occupying the bed. Bed 16 includes a sensor 118 which detects whether the mattress has been placed in a prevention mode, which is effective for preventing pressure sore formation on the patient. A currently available bed, having the above discussed features is the Advance 2000.RTM. by Hill-Rom-.RTM. Furthermore, bed 16 might include other mechanical/electrical systems related to patient care, and bed 16 may be retrofitted with sensors in accordance with the principals of the present inventions to detect other bed conditions and to provide other bed status information. To illustrate the operation of the present invention, the six sensed bed condition input signals of bed not down (BND), brake not set (BNS), prevention mode (PM), footrails not latched (FRNL), headrails not latched (HRNL), and bed exit system not armed (BENA) will be utilized in the detailed description of the invention. However, a person of ordinary skill in the art may utilize other status conditions which are sensed and processed in accordance with the principles of the present invention.

Referring to FIG. 4, all of the various sensors which sense bed status conditions are connected to a sensor hub 120 carried by the frame of the bed, preferably at the center of the bed. For example, the footrail and headrail sensors 25a, 25b, 27a, 27b are connected to hub 120 by lines 122 and 124, respectively. The bed exit system sensor 108 is coupled to hub 120 by line 126. The bed brake sensor 114 is coupled to hub 120 by line 115, while bed/mattress mode sensor 118 and bed position sensor 110 are coupled thereto by lines 119 and 111, respectively. Other status condition sensor lines, collectively illustrated as 130, may also be connected to hub 120. A plurality of hub output lines, indicated collectively by reference numeral 33, couple the hub signals as inputs to bed interface unit 35 at the headboard 100 of bed 16. Bed condition input signals might also be routed through hub 120 to the foot board 102 by lines 133, where they are displayed by a footboard bed control unit 134.

Figure 5:
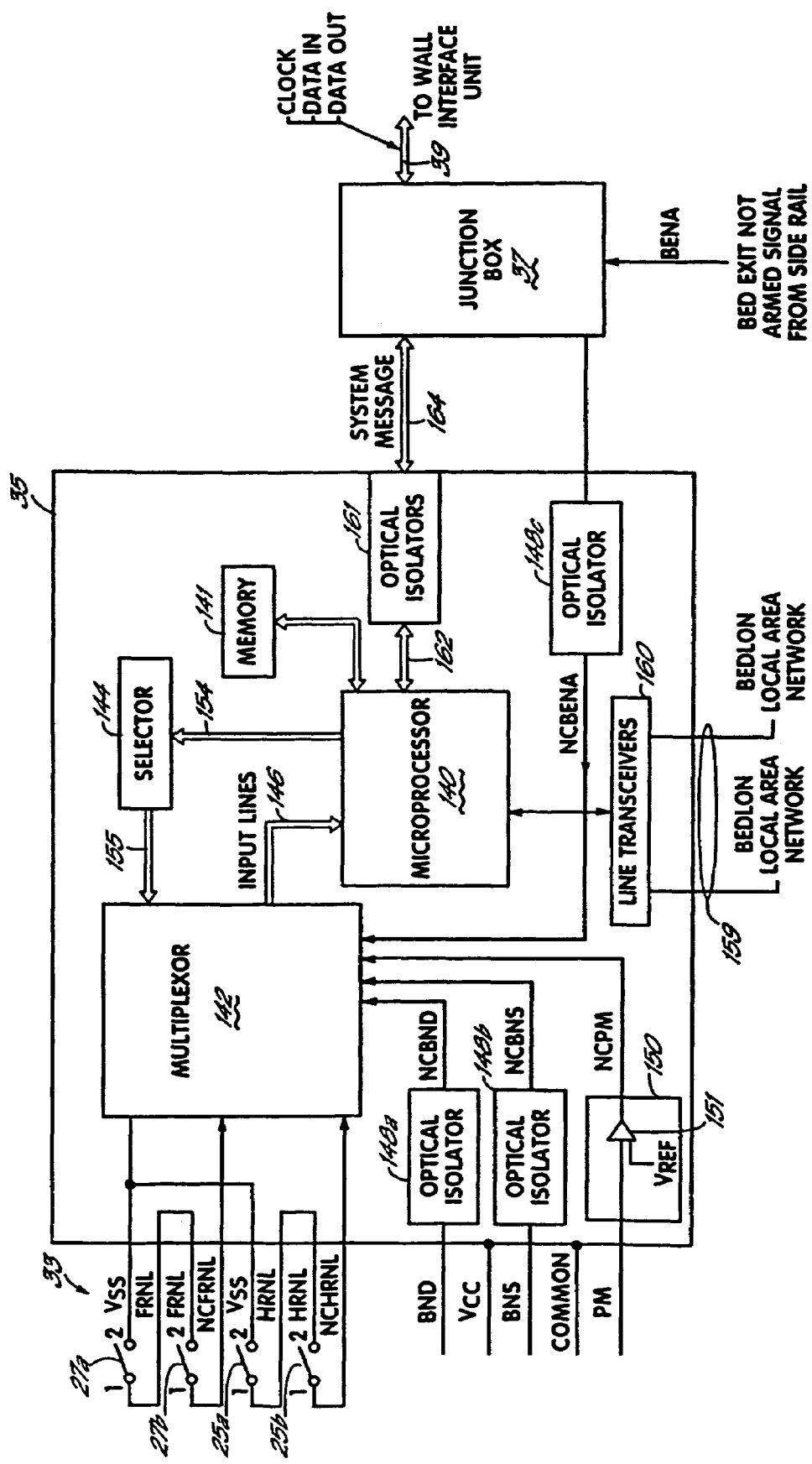
FIG. 5 is a schematic which depicts the electrical interconnections among the components of the bed status system of this invention.

FIG. 5 illustrates the electrical components and connections of the bed interface board 35. Bed interface board 35 utilizes a microprocessor 140 such as the MC143150 available from Motorola. Processor 140 is coupled to external memory 141, which may be an utilized as necessary in accordance with the invention. The various bed condition input signals or inputs 33 are routed into a multiplexor 142 which is controlled by selector 144 and processor 140 to input a selected bed signal to the processor 140 on input lines 146. Various of the bed condition inputs, such as BND, BNS, and BENA pass through optical isolators 148a, 148b, 148c (collectively 148) before reaching multiplexor 142. The optical isolators 148 prevent ground looping on the respective bed condition input lines which may cause false signals. With the optical isolators 148, there is no direct electrical connection between the selected bed signal condition input lines and the other electrical components of bed interface board 35. A suitable optical isolator for use in the present invention is a 4N35 available from Motorola.

The PM input line is sent through a signal conditioner circuit 150, which includes a comparator 151. The PM input has an operable voltage range which is compared to a reference voltage level V.sub.ref in order to determine whether the PM input is high or low. An LM393N comparator from Motorola is suitable for conditioner circuit 150. Power is supplied to the interface board on supply lines designated in FIG. 5 as V.sub.cc and common.

The bed condition inputs for the headrails (HRNL) and footrails (FRNL) are input directly to multiplexor 142. The HRNL input is connected in series with the pair of headrail sensors 25a, 25b. In a preferred embodiment, the sensors 25a, 25b are switches which, when closed, indicate that the respective rail is latched. When both switches 25a, 25b are closed (rails latched), the HRNL input signal, established by voltage V.sub.ss is pulled to a digital low level. When one or both of the switches is open, indicating that one or more rails are unlatched and in a down position, the HRNL input signal goes high. The bed input signal produced by the headrails and processed by the bed interface board is designated NCHRNL. The words "high", and "low" are utilized here and throughout the application to signify signal levels which are digitally high and low, respectively. Each monitored bed condition, such as the condition of the headrails, has a particular state or status. The condition status is determinative of the operational status of the particular sensor system, operational element or device that is being monitored on the bed. With respect to the headrails, the condition that is monitored is the position of the headrails, and the status of such a condition is either latched or unlatched. For example, the status of the headrails when the HRNL input signal is high is that the headrails are not latched; if the HRNL signal is low, the headrail status is a latched status. The monitored status of the various bed systems and devices should not be confused with the STATUS signals sent by the communicating nodes of the system, such as the interface board and the master station, as discussed in greater detail below. Similarly, the FRNL input is connected in series with the pair of footrail sensor switches 27a, 27b such that when both switches are closed (rails latched), the FRNL input is low, and when one or both switches are open (rails unlatched), the FRNL input is high. The input signal produced by the footrails is designated NCFRNL.

The condition indicated by the BND input signal is the position of the bed, such as that the bed is not in the down position. That is, the bed is in any position other than its lowest position, e.g., the bed has been raised to assist the patient to exit, to make the patient more comfortable, etc. When the bed is riot down, the status is indicated by the BND signal from system 110 going high. The output of the optical isolator 148a then goes low and is indicated by NCBND.

The condition of the bed brake is monitored by sensor 114. When the brake (not shown) of bed 16 is not set, the BNS input signal from sensor 114 indicates such a status by going high. The output of the optical isolator 148b goes low and is indicated by NCBNS.

When the bed exit system sensor 108 indicates that the bed exit system 29a, 29b has not been armed, the status is indicated by the BENA signal from sensor 108 which goes low. The output from optical isolator 148c then goes high and is designated NCBENA. As illustrated in FIG. 5, the BENA sensor signal might be taken from the siderail of the bed 16. Some models of the HILL-ROM Advance 2000.RTM. Bed allow activation of the bed exit system from the siderail.

When the mattress 31 of bed 16 has been placed in the prevention mode (the Advance 2000.RTM. bed has prevention mode and comfort mode), the PM input signal from sensor 118 is compared to a reference voltage V.sub.ref by comparater 151. If PM is from 4-4.5 volts, the output of the signal conditioner 150, designated NCPM, is low; however, if PM is from 2.5-3.5 volts, the output of the signal conditioner 150 is high and the condition status denotes that the bed is in a the prevention mode. The various signal levels for the sensed conditions are designated for a preferred embodiment of the present invention, but the invention is not limited to such signal levels for a detected bed condition, and the levels might easily be inverted or modified.

All of the sensed input signals which indicate the statuses of the monitored conditions are input to multiplexor 142. Processor 140 of the bed interface board 35 controls the multiplexor 142 through a selector 144. In accordance with the principles of the invention; the number of sensed input signals to multiplexor 142 might be increased to handle a greater amount of bed status information. Similarly, the number of selector inputs 154 and selector outputs 155 might be increased to accommodate a greater number of multiplexors for accessing and controlling a very large amount of bed status information. When the selected bed input signal to be monitored has been designated, the processor 140 sends a select signal on selector input lines 154 and the selector communicates with multiplexor 142 through output lines 155 to select a bed input signal (i.e., NCFRNL, NCBND, PM, etc.). The multiplexor 142 forwards the selected input signal to processor 140 through input lines 146. Processor 140 processes the various bed input signals 33 and forms a bed condition message to be sent to the wall interface unit 40 as described in greater detail hereinbelow.

In one embodiment of the invention, the bed input signals 33 are received as hard wired inputs by the bed interface board 35 from the various system sensors on bed 16.

Alternatively, a local area network protocol might be utilized as dictated by the chosen processor 140 utilized in bed interface board 35. For example, one possible processor protocol is available from Echelon and is designated LON (local operating network). The LON would be used to interface the different system sensors and status input signals of the bed to the bed interface board 35. The LON messages would be received by an appropriate line transceiver 160 from lines 159 and processed by microprocessor 140 and sent to the wall interface unit 40 in accordance with the present invention. Thus, the bed status system 11 of the present invention may be expanded by increasing the number of hardwired bed status inputs to interface board 35 or by increasing the number of nodes connected to the bed interface board through the LON.

The processor 140 processes the bed status input signals from the multiplexor 142 and creates a bed message depending upon the contents of the input signals. The bed message created by processor 140 is then sent through the bed junction box 37 to the wall interface unit 40 over serial datalink 39. The bed junction box 37 is also utilized to couple various bed functions and external devices, such as lighting and TV/radio, to the bed controls which are generally within easy reach of the patient. Optical isolators, collectively designated as 161, are coupled to input/output data lines 162 of processor 140 to prevent ground looping and to eliminate noise problems on the serial datalink 39. Preferably, each serial line is isolated. The input/output data lines 162 from processor 140 contain the messages from the bed 16 for communication with the patient/nurse communication system 10. The outputs of the optical isolators 161, designated by system message lines 164, are coupled through junction box 37 to the datalink 39 for communication with wall interface unit 40. Therefore, with the line isolators 161, there is no electrical connection between bed interface board 35 and the wall interface unit 40. A suitable isolator for the line isolators 161 is the 4N35 from Motorola.

The datalink 39 is preferably a five kilobit/second fully synchronous, point-to-point serial data interface. The interface requires three conductors, DATA IN, DATA OUT, and CLOCK and a master at one end and a slave at the other end. These three conductors DATA IN, DATA OUT and CLOCK are provided in datalink 39 and are approximately coupled through junction box 37 and isolators 161 to the input/output lines 162 of processor 140. In a preferred embodiment, the bed interface board 35 serves as the master, while the wall interface unit 40 serves as the slave. Compatible interfaces are supported by several manufacturers, such as Neurowire available from Echelon, SPI available from Motorola, and Microwire available from National Semiconductor. The standard datalink topology will allow a large variety of microprocessors to be utilized, both in the bed interface board 35, and the wall interface unit 40. The wall interface unit 40 is connected to a room station or patient station 41 by the intra-room network as illustrated in FIG. 3. The patient station 41 has full-duplex communications with the master station 46, and bed messages from the patient bed 16 are forwarded to the master station 46 through patient station 41. Other message types, besides bed messages, may be recognized by the patient station 41 and may be processed locally at the patient station 41.

Bed Status System Software Protocol

In a preferred embodiment of the interface protocol between the bed interface board 35 and the wall interface unit 40, the bed message structure has a message length fixed at ten bytes (80 bits). The message structure and the various fields contained therein are designated and configured as follows:

| FIELD | LENGTH | CONTENTS |
|---|---|---|
| MSG_TYPE | 1 byte | Indicates the type of message sent (e.g. whether it is a STATUS message or a BED_INPUTS or a BED_OUTPUTS message). |
| SEQUENCE_NUMBER | 1 byte | A number incremented by the sending node each time a message is sent. If a sequence number is not recorded by the system, this field may be left unutilized. |
| DATA_LENGTH | 1 byte | Indicates the number of active bytes LENGTH used in the data field of the message. The data field, DATA [6] of the message always allocates six bytes of data; however, any number of the six bytes may be implemented within the field for a particular message. |
| DATA [6] | 6 bytes | This field contains the data bytes of the message, e.g. bed inputs, identification numbers, bed type information. |
| CHECKSUM | 1 byte | This byte is used for message verification according to the CHECKSUM processing described further hereinbelow |

During operation, the bed interface board 35 polls every 250 milliseconds (+/−10 ms). Each poll provides 80 clock pulses from the bed interface board 35. At each poll, a message is sent from the bed interface board 35 to the wall interface unit 40 and from the wall interface unit 40 to the bed interface board 35. The messages will either be STATUS messages from the bed interface board 35 or wall interface unit 40, a BED_INPUTS message from the bed interface board to the wall interface unit, or a BED_OUTPUTS message from the wall interface unit 40 to the bed interface board 35 to control a particular system mechanism associated with the bed. When no BED_INPUTS or BED_OUTPUTS messages are sent, a STATUS message is automatically sent. A STATUS type message should not be confused with a BED_INPUTS message which provides the actual operational status or state of the monitored bed condition. STATUS type messages are indicative of the status of a particular communication node and whether it is properly communicating with the system.

With the message protocol of the bed status system 11, there are essentially four message combinations that are utilized. If the bed interface board 35 and wall interface unit 40 are both idle, then each will send STATUS messages back and forth to each other during each poll. If the bed interface board 35 sends a BED_INPUTS message, the wall interface unit answers with a STATUS message indicating that the BED_INPUTS message was received properly or was not received properly and should be resent. Similarly, the wall interface unit 40 may send a BED_OUTPUTS message to the bed, and the bed interface board will answer with a STATUS message. Finally, both the interface board 35 and interface unit 40 may send BED_INPUTS, BED_OUTPUTS messages, respectively, and on the next poll, the corresponding receiving nodes will answer with a STATUS message.

The STATUS message indicates to the sending node the status of the receiving node or how the last sent message was received by the receiving node. The term "node" in the present context is utilized to describe either the bed interface board or the wall interface unit. The STATUS message may indicate one of four conditions at the sending node of the message, such as the bed interface board node. When a STATUS message is sent, the MSG_TYPE field will indicate that the message is a STATUS message. The data contained in the DATA [6] field will then indicate the actual status of the sending node (e.g. the bed interface board 35). The actual status data is only one byte long and if the byte is all zeros, this is designated a TYPE_ZERO status. The TYPE_ZERO status is essentially a handshake status which indicates to one of the nodes that it may communicate with another particular node. That is, it may indicate to the bed interface board 35 that the wall interface unit is connected to the system and will communicate. If the DATA[6] field byte is not all zeros, and if the first bit of the byte is set, the node status is designated as an acknowledge status or ACK. That is, the STATUS message indicates that the receiving node properly received the last message. If bit two of the byte is set, the STATUS MESSAGE is designated as a not acknowledge or NAK message. If bit three of the status data byte is set, the status message is designated as a RESET message. The result of a RESET message is discussed further hereinbelow. Therefore, the STATUS messages are ACK, NAK, TYPE_ZERO, and RESET. Every time that a parameter in the STATUS message changes, the message should be resent and should take priority over any non-STATUS message.

Each time a BED_INPUTS or BED_OUTPUTS message is sent (i.e., each time on non-STATUS message is sent) by a sending node over datalink 39, an ACK status message must be received by the sending node from the message receiving node before that sending node can send another message. If the sending mode receives a NAK message from the message receiving node, this implies that the last message was received incorrectly by the message receiving node. The sending node then resends the last sent message. The nodes will only respond to the ACK and NAK messages if the last sent message was a non-STATUS message, such as a BED_INPUTS message. Otherwise the nodes will just continue to send STATUS messages back and forth.

If no ACK or NAK message is received within a certain amount of time, the node may time-out and reset itself. Upon resetting, the node sends a RESET message, and on the next poll, the node will send the messages that it originally sent on power up of the system, which is discussed in greater detail below. Therefore, all sent messages except for STATUS messages require an ACK-type STATUS message from the receiving node. If the sending node times out before receiving an ACK message, the node resets itself. Preferably, the wall interface unit 40 gives first and highest priority to any hardwire nurse calls from the bed interface board 35, such as nurse calls coming from the pillow speaker 44. The bed interface board 35 will wait until the wall interface unit 40 is not processing high priority calls before messages can be forwarded. A message of all zeros or all ones; from a sending node will be ignored by the receiving node and a NAK message will not be generated.

The bed interface board 35 sends various bed information messages (i.e. BED_INPUTS messages) to the wall interface unit 40 during operation of the bed status system 11 of the invention. In one embodiment of the invention, the available BED_INPUTS messages are designated BED_TYPE, ID_NUMBER BED_INPUTS_UPDATE and INPUTS_MSK. The BED_TYPE message informs the wall interface unit 40 of the type of bed connected to the system. As a result, the master station 46 may be programmed to display different screens for different model beds according to the various bed information messages that are sent by the system. In a BED_TYPE message, the MSG_TYPE field indicates that the data DATA [6] field contains data about the type of bed connected to the system as a node. The bed type is indicated by one data byte within the DATA [6] field. For example, the data byte may contain a value corresponding to the Advance 2000.RTM. bed available from Hill-Rom. RTM., while another value would indicate the presence of an Advance 1000.RTM. bed, also available from Hill-Rom. RTM. In that way, information from various different types of beds connected to the system is processed accordingly.

An ID_NUMBER message informs the wall interface unit 40 and system 10 of the unique identification number associated with a particular bed. This number may be cross-referenced to a serial number associated with the bed 16 or may actually contain the bed serial number. Thus, the bed status system 11 tracks individual beds throughout the system. When an ID_NUMBER message is sent, the MSG_TYPE field indicates that the bytes in the DATA [6] field contain a unique identification number. Preferably, all six bytes of the DATA [6] field are utilized to indicate the identification number of the bed. The identification number is unique to each bed interface board 35, and therefore, if the bed interface board 35 is ever replaced, a new number would be associated with the bed 16.

The ID_NUMBER message provides automatic retrieval of serial number information for a bed and may be forwarded to a master station or other processing device in both the maintenance department and the accounting department of a hospital. The maintenance personnel will then be able to record and track a particular bed for record-keeping purposes to determine the maintenance or replacement schedule for the bed, as well as to determine whether the particular bed may need an upgrade in its capabilities as discussed further hereinbelow. Further, the accounting personnel will have accurate recordkeeping information regarding the use of the beds for both billing purposes and occupancy monitoring to insure efficient and constant use of the beds and reduced bed down-time.

A bed inputs mask message designated INPUTS_MASK is also sent from the bed interface board 35 to the wall interface unit 40. The INPUTS_MASK message corresponds to a hardwired bed inputs mask which preferably is set at the time of manufacturing of the bed interface board for a particular bed 16 and is saved in processor memory. The INPUTS_MASK message is indicated by the MSG_TYPE field and three bytes of the DATA [6] field are dedicated to the message. The INPUT_MASK message informs the wall interface unit 40 and system 11 of the available bed conditions which are valid and may be sensed on the bed corresponding to the hardwired inputs 33 from the bed 16. For example, the INPUTS_MASK message might indicate that the headrail-not-latched (HRNL), footrail-not-latched (FRNL), and brake-not-set (BNS) conditions are available as bed inputs to the system from the particular type of bed providing the message. Since the bed inputs mask is preferably processor hardwired at the time of manufacturing, any changes to the available bed condition inputs should be incorporated into an updated bed inputs mask. The bit locations of one byte in the DATA [6] field indicate the available bed inputs for a particular bed. In a preferred embodiment, the availability of condition BENA (bed-exit-not-armed) as an input is indicated at bit position one of the first byte of the DATA [6] field. Similarly, condition PM is indicated at bit position two, BND is indicated at bit positioned three, BNS is indicated at bit position four, FRNL is indicated at bit position five and HRNL is indicated at bit position six. The availability of other bed input conditions might be indicated at other bit positions in the INPUTS_MASK message. One particular benefit of the INPUTS_MASK message is that it provides information regarding the capabilities of the bed and may be routed to a maintenance facility in the hospital for determining which beds may be used for particular purposes. Maintenance personnel are able to be apprised that a particular bed in the wing of a hospital may need a capability that is not currently available and that they should either retrofit the bed with the capability or replace a particular bed with a different bed. Furthermore, maintenance personnel are provided with an automatic indication of the location and capabilities of each bed should it be necessary to upgrade a particular feature for all of a particular type of bed.

The data to be sent in the BED_TYPE, ID_NUMBER, INPUTS_MASKS messages is stored in memory. In a power-up or reset condition of the bed status system 11, the respective information for the bed is retrieved from memory and is sent in the respective messages to the wall interface unit 40, and ultimately the master station 46. Further at power-up or reset, any timers of the nodes are preferably initialized, internal processing indices of the node processors are initialized and message request registers of a node are initialized. Preferably, flags are set in processor 140 to send the BED_TYPE, ID_NUMBER and INPUTS_MASKS messages upon power-up, and corresponding flags are reset when the messages have been sent. An interval variable might be utilized by the processor 140 to keep track of how many messages are sent to ensure that all messages on power-up or reset are sent. These three messages are also sent upon a node reset. As discussed above, whenever a bed information message is sent, the sending node, such as the bed interface board 35 waits to receive an ACK or NAK message. At the time the bed message is sent, the node has an internal timer which begins its count. If an ACK or NAK message is not received within the predetermined time out count, the node resets and sends a RESET message to the receiving node. Upon the reset of the bed interface board 35, the BED_TYPE, ID NUMBER, and INPUTS_MASK messages are again sent to the wall interface unit upon successive poles, similar to a power-up condition. In a preferred embodiment of the invention, processor 140 keeps track of a variable which decrements each time a power-up or reset message is sent in order to determine that all of the necessary messages have been sent. Furthermore, when each of the messages is sent or reset, the requisite flag corresponding to the message is also cleared.

After a power-up or reset condition occurs, and all of the necessary initialization messages related to the particular patient bed 16 have been sent to wall interface unit 40, the bed interface board 35 and wall interface unit 40 are then ready to send and receive messages corresponding to the various bed inputs 33 which are sensed on the patient bed 16. The conditions that are sensed by the status system for any particular bed is determined by the inputs mask of the bed processor 140 and the INPUTS_MASK message. Upon power-up or reset, each node must send a status message first. After a node receives a status message, then initialization messages, e.g. BED_TYPE, ID_NUMBER and INPUTS_MASK are sent.

A BED_INPUTS_UPDATE message indicates the status of one or more the hardwired bed inputs 33 which reflect a particular sensed condition on the bed 16. As discussed above, the following bed condition inputs are sensed by an embodiment of the present invention: prevention mode mattress condition (PM), bed exit arming condition (BENA), bed position condition (BND), bed brake condition (BNS), footrail condition (FRNL), and headrail condition (HRNL). In accordance with the principles of the present invention, other bed conditions might also be sensed and provided as inputs 33 to the bed interface board 35. The BED_INPUTS_UPDATE message is indicated by the value in the MSG_TYPE field and currently utilizes 1 byte of the data [6] field of the message format. However, six bytes are available depending upon the number of bed conditions which are sensed. In a preferred embodiment of the invention, the bit positions in the first data byte of the DATA [6] field of the BED_INPUTS_UPDATE message are configured as follows:

| Sensed Condition | Bit Position | Logic Level |
| --- | --- | --- |
| Bed Exit Not Armed (BENA) | One | Logic One |
| Prevention Mode (PM) | Two | Logic One |
| Bed Not Down (BND) | Three | Logic Zero |
| Brake Not Set (BNS) | Four | Logic Zero |
| Footrail Not Latched (FRNL) | Five | Logic One |
| Headrail Not Latched (HRNL) | Six | Logic One |

Therefore, the value of a selected bit indicates the status of a sensed bed condition. For example, if one of the footrails 19a, 19b of bed 16 has been unlatched and placed in a down position, the appropriate sensor 27a, 27b will sense the unlatched condition and send a signal on the FRNL hardwire input 33. Processor 140 then reads the NC FRNL signal from multiplexor 142 into bit position five of a data byte in the BED_INPUTS_UPDATE message which is set at logic One. If the bed mattress 31 is in the prevention mode to prevent bed soreness of patient 12, the processor 140 sets bit position two to logic One in the BED_INPUTS_UPDATE message. Similarly, the other bit positions are set to logic ones or zeros depending upon the sensed conditions. Processor 140 sends a BED_INPUTS_UPDATE message each time one of the hardwire inputs 33 has changed. Thus, the system 11 continually updates the status of the patient bed 16.

The message protocol of the bed status system 11 not only senses the status of various bed conditions but also might be utilized to control one or more of the functions on the bed. For example, if the bed exit sensor 108 indicates that the bed exit system pads 29a, 29b have not been armed, a nurse or other attending personnel may decide that they would like to arm the system in order to determine whether a patient has left the bed. To arm the bed exit system, the master station 46 creates a message to arm the bed exit. The BED_OUTPUT message is then sent through 110 board 70, patient station 41, wall interface unit 40, and then datalink 39, to the bed interface board 35. Processor 140 of the bed interface board 35 might be equipped with an appropriate transceiver and I/O circuitry (not shown) in order relay the message to the sensor 108 of bed 16 and to arm the bed exit system. Therefore, through the message protocol the bed status system 11 of the present invention, various functions on the bed might be controlled from the master station 46.

Each message is sent between the bed interface board 35 and wall interface unit 40 either over the DATA IN or DATA OUT lines of datalink 39, with the necessary timing provided by the CLOCK line.

To determine that a sent message is accurately received by the receiving mode, parity checking routine might be utilized. Such parity routines are known by persons of ordinary skill in the art. The present invention includes the 1 byte CHECKSUM field in the message for such verification. In an embodiment of the invention, a simple routine is utilized by making the CHECKSUM byte equal to the inverted sum of the other nine message bytes plus one (1). Then, when the message is received by the receiving mode, the nine message bytes are added to the CHECKSUM byte and any carries from the addition are ignored. If the result is zero (0), then the message was properly sent. If the result is other than zero, then the message should be sent again. Since such a simple routine will not work when the sent message begins as all zeros, the CHECKSUM byte might be given an offset value to make it other than zero.

Figure 7:
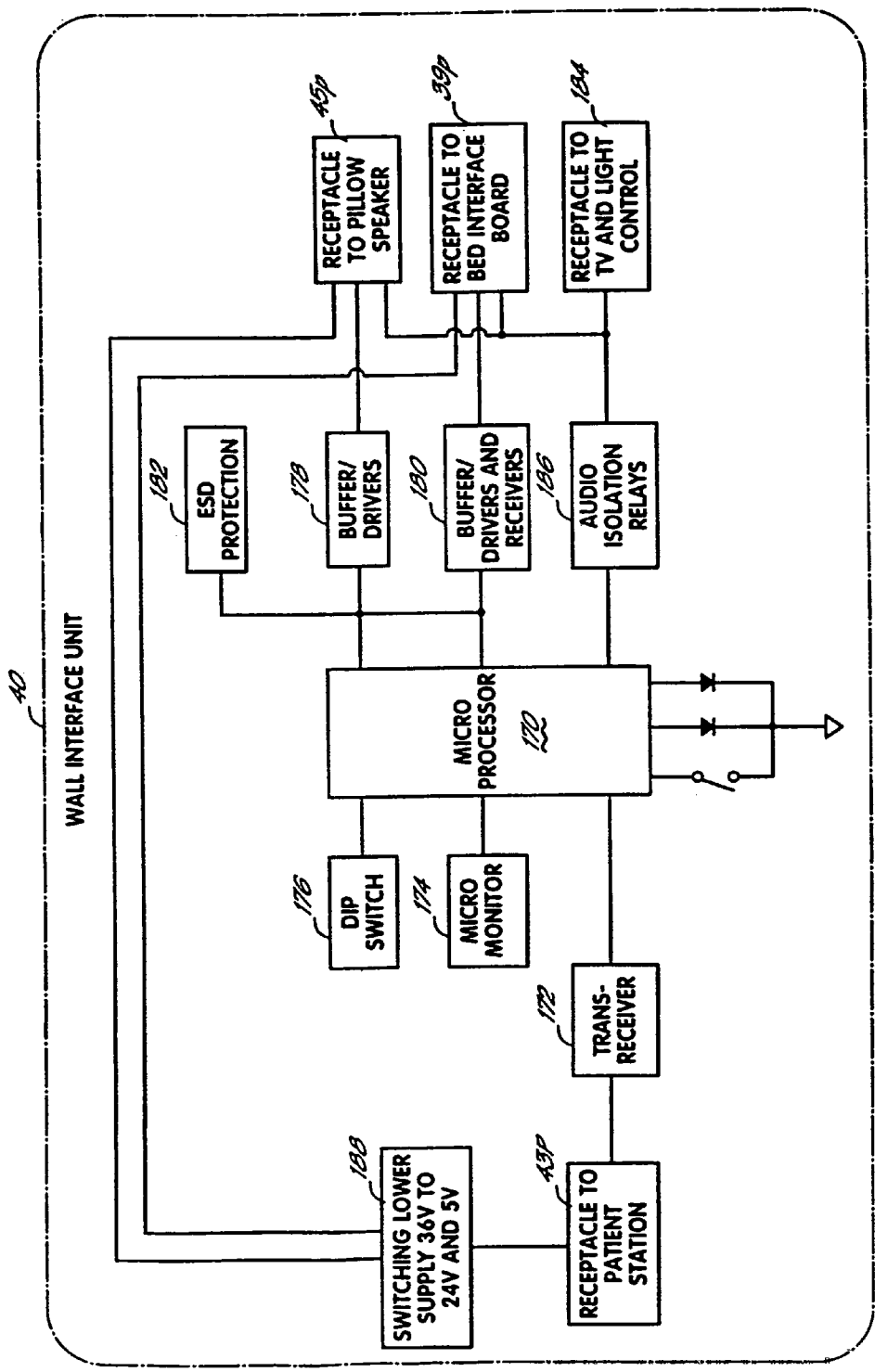
FIG. 7 is an electrical schematic which shows electrical connections among components of the patient station for a patient/nurse communication system integrated with the bed status system of this invention.

FIG. 7 illustrates the various electrical components and interconnections of a wall interface unit 40 in accordance with the present invention. The wall interface unit 40 is run by a microprocessor 170 such as an 8052 from Intel. The patient stations 41 are coupled to processor 170 by appropriate receptacles 43p, an RS485 serial link 43 and an appropriate transceiver 172. A micromonitor 174 controls the operation of processor 170 while dip switch 176 provides the address for the wall interface unit in a multiple bed room. The pillow speaker 44 is coupled to processor 170 through an appropriate receptacle 45p and the necessary buffers and drivers 178 as recognized by a person of ordinary skill in the art. The bed interface board 35 is somewhat similarly coupled to the processor 170 through buffer/driver/receiver circuitry 180 and receptacle 39p for proper communication between the wall interface unit 40 and the bed interface board 35. The circuitry 180 preferably contains optical isolators (not shown), similar to isolators utilized in the bed interface board, to isolate the DATA IN, DATA OUT and CLOCK lines between the bed interface board 35 and the wall interface unit 40. Both the pillow speaker buffer/driver unit 178 and bed interface buffer/driver/receiver unit 180 are connected to electrostatic discharge (ESD) protection circuitry 182 to protect the wall interface unit from stray discharge from the bed. Television and light controls (not shown) for the room may also be routed through the wall interface unit 40 by an appropriate receptacle 184. An audio isolation relay 186 should preferably be used between receptacle 184 and processor 170 to provide an override of the television and other entertainment audio by a nurse call audio when a nurse calls the room. A switching power supply 188 is also connected to the pillow speaker receptacle 45p, bed interface board receptacle 39p, and patient station receptacle 43p for proper operation of the receptacles.

When the bed and bed interface board 35 sends a STATUS or BED INPUT type message, the wall interface unit 40 receives the message and extracts the contacts of the MSG_TYPE, DATA_LENGTH and DATA [6] fields after it has received a valid parity checking indication. The extracted message contents are then repackaged into another protocol utilized between the wall interface unit 40 and patient station 41. The message contents are again repackaged in the protocol utilized to send the messages from the patient station 41 to the master station 46 through the PBX 62. The various components of the patient station 41 and master station 46 and the protocols between them as well as the protocols between the patient station 41 and wall interface unit 40 are described in greater detail in the parent application entitled Patient/Nurse Call System. When the wall interface unit 40 receives a bed message, the message is routed to the master station 46 similarly to the way in which a message from the pillow speaker 44 is sent to the master station 46.

The master station 46 displays the bed message and the status of the bed 16 and its various systems on display 47 when selected by attending personnel. FIG. 8 displays one possible screen arrangement 190 for the display 47 to illustrate bed status to attending personnel. Under the INFO menu 192 shown at the bottom of screen 190 the bed status may be selected and is displayed in various screen fields. For example, the screen of FIG. 8 illustrates that the bed in Room 103A has its exit system armed 194, one or more of the side rails in a down position 196, the bed brakes set 198, the height of the bed in an upward position 200 and the mattress in a comfort mode 202. Other conditions which are detected might also be displayed in accordance with the principles of the present invention. As will be understood by a person of ordinary skill in the art, the available bed status information is stored in memory at the master station for retrieval when desired.

Patient/Nurse Status System Operation

At start up, the operational software which actually controls the patient station 41 is dynamically downloaded from the master station 46. This allows software updates and modifications to be implemented without having to change a PROM in the patient stations 41. All patient stations 41 have a small program called the LOADER which is permanently stored in the 8K of program space on the 8752 microprocessor that serves as the CPU for each station. The main function of the LOADER program is to receive the downloaded operational software, which is stored in the 64K of RAM space of the patient station 41 as it is received. When the download is complete, the LOADER program first performs a checksum test to determine if the downloaded software is error-free, and if so, then switches the processors s program execution area to RAM, thereby beginning execution of the downloaded program. This allows for the running of a much larger program than could fit into the 8752's on-chip program area. Currently, the RAM executable program area is configured to be approximately 48K in size, with an additional 16K of RAM reserved for data space.

Three hardware/software components are involved in the download process (in addition to the PBX 62), as well as three data channels. The hardware/software components are the patient station 41, the loader card 57 and the master station PC 52. The data channels are the D-channel, the B-channel, and the RS-232 serial datalink. The loader card 57 resides in the master station PC 52 and communicates therewith over the RS-232 link. It also communicates with the PBX 62. To the PBX 62, it looks like just another patient station 41. The binary image of the software to be downloaded to the patient station 41 is first transmitted to the loader card 57 over the serial datalink. The loader card 57, upon receipt of the appropriate command from the master station PC 52, then transmits the binary image of the station software over the B-channel, which operates normally as the audio channel and which is much faster than the D-channel. The D-channel is used by all three components for synchronization and control. The loader card 57 communicates with the master station PC 52 over a serial datalink. Actually, the loader card 57 looks like a serial adapter card to the master station PC 52 and is configured to communicate with the master station PC 52 over the MS-DOS COM4 channel at 19.2 k baud, with 8 data bits, no parity bits, and 1 stop bit.

When the application software for the system 10 boots up on the master station PC 52, it looks for a file which contains the executable code to be used in the patient station 41. This file is a binary image of the downloadable station software. It is transmitted to the loader card 57 in 256 byte blocks, plus a relatively small header block at the start. This transmission is essentially performed in the background, so that the system 10 can perform other functions at the same time. The downloading to the loader card 57 usually takes about 30 seconds.

When the loader card 57 receives the last block, i: calculates an EXCLUSIVE-OR sum and a normal sum of a data received and compares the 2 sums with the 2 received checksums. If they match, it sends back an ASCII 'O' followed by an ASCII 'OR' to the software of the master station 46. This constitutes an acknowledgement and the master station 46 considers the loader card 57 ready to download to the patient stations 41. The loader card 57 now has the binary image.

In the downloading process, the D-channel is used for synchronization and control, as well as for requests and responses. When a patient station 41 is first powered up, it performs a test to determine if it has downloaded software present (RAM is kept electrically charged for a few hours when there is no power to the station 41, so the station 41 software in RAM can be retained with no external power) and performs a checksum test to determine if the software is valid. If so, the station 41 begins running the software in RAM. If it has no software in RAM or determines that the software is invalid, it begins sending 'download request' messages over the D-channel, to the master station 46. By default, these requests are sent once every 60 seconds. When the software at the master station 46 receives a request, if it is not currently waiting for a download to another station 41 to complete, it initiates the download process by sending a 'prepare for download' message to the station 41 and then sending a 'begin download' message to the loader card 57. It then opens a special data channel B1 between the station 41 and the loader card 57 to transmit the binary data from the loader card 57 to the patient station 41.

When the station 41 receives a 'prepare for download' message it sets a timer allowing about 15 seconds for completion of the downloading. If the station 41 receives the complete download, it resets the timer, and then performs a checksum test on the downloaded software which it now has sorted in RAM. If the test passes, the station 41 sends back a D-channel 'download successful response' message to the software of the master station 46, and the station 41 switches execution to the software in RAM. If the checksum test fails or if the station 41 timed out, it sends back a 'download response' message with an error code and subsequently resumes sending 'download request' messages until downloading succeeds.

The B-channel is normally used for audio communication in this system 10. Audio is converted to digital signals and then transformed by the PBX 62, resulting in a difference between the digital signal transmitted on the B-channel by one station 41 and the digital signal arriving at a destination station 41. In the downloading process, the B-channel is used to transmit a binary image from the loader card 57 to the station 41 being downloaded to, because data can be transmitted much faster over the B-channel than the D-channel. The B-channel can transmit 64000 bits per second, whereas the D-channel can effectively transmit only about 2000 bits per second.

However, to use the B-channel to transmit data, no PBX processing can be performed on the signal. So when an audio channel is opened between the loader card 57 and the patient station 41 to be downloaded to, the system 10 must essentially tell the DXP 62 to pass the digital audio signal through without processing it.

Also, when the station 41 receives the D-channel 'prepare for download' message, it sets itself up to temporarily route the incoming audio bits to a LOADER software download routine, instead of to the speaker, which is where audio is normally routed.

The protocol used for the transmission of the audio data from the loader card 57 to the patient station 41 is similar in some respects to the transmission of the data from the master station PC 52 to the loader card 57 over the serial channel. There is a header sent before the rest of the data and the actual binary image software data is transmitted 256 bytes at a time.

There the similarity ends. Part of the difference is due to the nature of the transmission medium. The serial channel is asynchronous, meaning that at any given moment, a serial byte may be in the process of being transmitted, but for long periods the serial channel may be idle. The audio channel, on the other hand, is synchronous, and is essentially never idle. Therefore, a special preamble is used to help insure that each patient station 41 recognizes the start of the header block, and another preamble is used for each 256 byte data block. Also, each data block has a checksum appended to it, which incorporates the loading address for that block. Finally, if the patient station 41 determines that the header block or a subsequent data block has errors in it because the block checksum test failed, it sends a "no acknowledgement" message to the loader card 57, and that block is retransmitted. A block may be retransmitted a maximum of six times before the process fails.

Operational interfaces for interacting with the system 10 at the master station 46 and at the patient stations 41, respectively, may be established or created in accordance with the needs or specifications of the facility. More specifically, particulars of the operational interface will determine what appears on displays 47 and 97 at the master station 46 and the patient station 41, respectively, and how these displays change via selective rotation and depression of the control wheels 50 and 96.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

We claim:

1. A bed monitoring system to remotely monitor the status of a patient bed, the bed monitoring system comprising:
   a bed status system coupled to a patient bed, the bed status system configured to monitor a first monitored condition of a patient bed to which it is coupled, monitor a second monitored condition of a patient bed to which it is coupled, and to generate a bed status message indicating the status of one of the first monitored condition and the second monitored condition; and
   a master station remote from the patient bed, the master station operatively coupled to the bed status system of the patient bed to receive bed status information related to the bed status message, wherein the bed status message includes a bed type field identifying the type of bed corresponding to the bed status message, the master station operable to determine the bed type of the patient bed based on the bed type field.

2. The bed monitoring system of claim 1, wherein the bed status signal includes a bed identifier field uniquely identifying the patient bed, the master station operable to determine the identity of the patient bed corresponding to the bed status message based on the bed identifier field.

3. The bed monitoring system of claim 1, wherein the bed status message indicates whether the patient bed is occupied.

4. The bed monitoring system of claim 1, wherein the bed status system and the content of the bed status message varies depending on the bed type of the patient bed.

5. The bed monitoring system of claim 1, wherein the bed status system is further configured to monitor a plurality of monitored conditions, the bed status message indicating the status of at least one condition of the plurality of monitored conditions; and the bed status system is further configured to generate content for the bed status message based on a selector signal, the selector signal indicating which of the conditions of the plurality of monitored conditions of the patient bed are to be included in the bed status message.

6. The bed monitoring system of claim 5, wherein the selector signal is generated at the master station.

7. The bed monitoring system of claim 1, further comprising a plurality of processing stations, each station of the plurality of processing stations having a receiving range and being configured to receive the bed status message from any patient bed within the receiving range, and to process the bed status messages to generate a station message indicating the status of the monitored condition for the any patient bed within the receiving range.

8. The bed monitoring system of claim 1, wherein the bed status system includes a patient exit detection system, and the bed status message indicates when a patient exit is detected.

9. The bed monitoring system of claim 1, wherein the bed status system includes at least one sensor having a staff controlled setting, and the master station is operable to send a setting control message to the bed status system, and the bed status system of the patient bed is operable to set the at least one sensor having a staff controlled setting based on the setting control message.

10. The bed monitoring system of claim 9, wherein the at least one sensor having a staff controlled setting is a patient exit detection system having the staff controlled settings of armed and disarmed.

11. The bed monitoring system of claim 1, wherein the master station includes a bed status indicator, the master station being configured to indicate the status of the monitored condition on the bed status indicator.

12. The bed monitoring system of claim 11, wherein the bed status indicator is a display device and the bed status information for the patient bed is viewable on the display device.

13. The bed monitoring system of claim 1, wherein the first monitored condition relates to a person at least partially supported by the patient bed, and the second monitored condition relates to a function of the bed.

14. The bed monitoring system of claim 1, wherein the first monitored condition relates to a first bed and the second monitored condition relates to a second bed.

15. The bed monitoring system of claim 1, wherein the bed status message indicates the status of the first monitored condition and the second monitored condition.

16. The bed monitoring system of claim 1, further comprising a selector signal generated by one of the bed status system and the master station to select content for the bed status message.

17. A bed monitoring system for locating a patient bed, including:
   a bed signal generator coupled to the patient bed, the bed signal generator generating a bed status message including a bed identifier unique to the patient bed to which it is coupled;
   a locating station located in each of a plurality of monitored locations, each locating station being configured to receive the bed status messages from any patient beds within the monitored location associated with the Locating station, and to generate a station status message including information from the bed status messages and indicating the location of the locating station; and
   a master station remote from the patient bed, the master station being operatively coupled to each of the locating stations to receive the station status messages generated by the locating stations;
   wherein the master station processes the station status messages to determine the location of the patient bed.

18. The bed monitoring system of claim 17, further comprising a bed status system coupled to the patient bed, the bed status system configured to monitor a monitored condition of the patient bed, and the bed status message including the status of the monitored condition of the patient bed.

19. The bed monitoring system of claim 17, wherein the patient bed further comprises a patient exit detection system, and the bed status message indicates when a bed exit is detected.

20. The bed monitoring system of claim 17, wherein the patient bed monitors whether the bed is occupied, and the bed status message indicates whether the bed is occupied.

21. The bed monitoring system of claim 17, wherein the master station further comprises a display device and the location of the patient bed is viewable on the display device.

22. The bed monitoring system of claim 21, wherein the bed status message includes a bed type field identifying the type of bed corresponding to the bed status message, the master station being operable to determine the bed type of the patient bed based on the bed type field, and the location and the bed type of the patient bed can be displayed on the display device.

23. A bed monitoring system for locating each of a plurality of patient beds, including:
   a bed status system coupled to each bed of the plurality of patient beds, each bed status system monitoring a monitored condition of the bed to which it is coupled, and generating a bed status message indicating the status of the monitored condition of the bed to which it is coupled;

a locating station located in each of a plurality of monitored locations, each locating station being configured to receive the bed status messages from the plurality of patient beds within the monitored location associated with the locating station, and to generate a station status message including information from the bed status messages and indicating the location of the locating station; and a master station remote from the plurality of patient beds, the master station being operatively coupled to each of the locating stations to receive the station status messages generated by the locating stations.

24. The bed monitoring system of claim 23, wherein each bed status system monitors whether the bed to which it is coupled is occupied, and the bed status message indicates whether the patient bed is occupied, the master station being operable to determine the locations of at least one of unoccupied patient beds and occupied patient beds.

25. The bed monitoring system of claim 23, wherein the bed status signal includes a bed identifier uniquely identifying each bed of the plurality of patient beds, the master station operable to determine the identity of the patient bed corresponding to the bed status message based on the bed identifier.

26. The bed monitoring system of claim 25, wherein each bed status system monitors whether the bed to which it is coupled is occupied, and the bed status message indicates whether the patient bed is occupied, the master station being operable to determine whether any bed of the plurality of patient beds is occupied.

27. The bed monitoring system of claim 25, wherein at least one bed of the plurality of patient beds further comprises a patient exit detection system, and the bed status message for each such bed indicates when a bed exit event is detected, the master station being operable to indicate the location of the patient bed of the plurality of patient beds that detected the bed exit event.

28. The bed monitoring system of claim 25, wherein the bed status message includes a bed type identifier identifying the type of bed corresponding to the bed status message, the master station operable to determine the bed type of each bed of the plurality of patient beds based on the bed type identifier.

29. The bed monitoring system of claim 28, wherein the format of the bed status message varies depending on the bed type of the patient bed, the master station operable to process the bed status message based on bed type.

30. The bed monitoring system of claim 17, wherein the bed status system is further configured to monitor a plurality of monitored conditions, the bed status message indicating the status of at least one condition of the plurality of monitored conditions, and the bed status system generating content for the bed status message based on a selector signal, the selector signal indicating which of the conditions of the plurality of monitored conditions of the patient bed are to be included in the bed status message.

31. The bed monitoring system of claim 17, wherein the bed status system includes at least one sensor having a staff controlled setting, and the master station is operable to send a setting control message to the bed status system of any bed of the plurality of patient beds, and the bed status system of the any bed of the plurality of patient beds is operable to set the at least one sensor having a staff controlled setting based on the setting control message.

32. The bed monitoring system of claim 17, wherein the master station further comprises a display device and the location of each bed of the plurality of patient beds is viewable on the display device.

33. The bed monitoring system of claim 32, wherein the bed status message includes a bed type field identifying the type of bed corresponding to the bed status message, the master station being operable to determine the bed type of the patient bed based on the bed type field, and to display the location and the bed type of each bed of the plurality of patient beds on the display device.

* * * * *